United States Patent
Chinta et al.

(10) Patent No.: US 10,293,331 B2
(45) Date of Patent: *May 21, 2019

(54) SUPPORTED NANO SIZED ZEOLITE CATALYST FOR ALKYLATION REACTIONS

(71) Applicant: FINA TECHNOLOGY, INC., Houston, TX (US)

(72) Inventors: Sivadinarayana Chinta, Missouri City, TX (US); Joseph Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 406 days.

This patent is subject to a terminal disclaimer.

(21) Appl. No.: 15/042,313

(22) Filed: Feb. 12, 2016

(65) Prior Publication Data
US 2016/0158737 A1    Jun. 9, 2016

Related U.S. Application Data

(63) Continuation of application No. 13/712,380, filed on Dec. 12, 2012, now abandoned.

(60) Provisional application No. 61/581,635, filed on Dec. 30, 2011.

(51) Int. Cl.
| | | |
|---|---|---|
| *B01J 29/06* | (2006.01) | |
| *B01J 29/08* | (2006.01) | |
| *B01J 29/40* | (2006.01) | |
| *B01J 29/70* | (2006.01) | |
| *B01J 35/02* | (2006.01) | |
| *C07C 2/66* | (2006.01) | |
| *C07C 2/86* | (2006.01) | |
| *B01J 35/00* | (2006.01) | |
| *B01J 37/04* | (2006.01) | |
| *B01J 37/34* | (2006.01) | |
| *B82Y 35/00* | (2011.01) | |
| *B01J 29/16* | (2006.01) | |
| *B01J 29/48* | (2006.01) | |
| *B01J 29/78* | (2006.01) | |
| *B82Y 30/00* | (2011.01) | |

(52) U.S. Cl.
CPC ............. *B01J 29/084* (2013.01); *B01J 29/40* (2013.01); *B01J 29/7007* (2013.01); *B01J 29/7034* (2013.01); *B01J 29/7038* (2013.01); *B01J 35/0013* (2013.01); *B01J 35/023* (2013.01); *B01J 37/04* (2013.01); *B01J 37/341* (2013.01); *C07C 2/66* (2013.01); *C07C 2/864* (2013.01); *B01J 29/08* (2013.01); *B01J 29/085* (2013.01); *B01J 29/16* (2013.01); *B01J 29/405* (2013.01); *B01J 29/48* (2013.01); *B01J 29/7057* (2013.01); *B01J 29/7084* (2013.01); *B01J 29/7088* (2013.01); *B01J 29/7815* (2013.01); *B01J 29/7869* (2013.01); *B01J 29/7876* (2013.01); *B01J 2229/32* (2013.01); *B01J 2229/42* (2013.01); *B01J 2229/64* (2013.01); *B82Y 30/00* (2013.01); *B82Y 35/00* (2013.01); *C07C 2529/08* (2013.01); *C07C 2529/12* (2013.01); *C07C 2529/14* (2013.01); *C07C 2529/16* (2013.01); *C07C 2529/70* (2013.01); *C07C 2529/74* (2013.01); *C07C 2529/76* (2013.01); *C07C 2529/78* (2013.01); *Y10S 977/773* (2013.01); *Y10S 977/779* (2013.01)

(58) Field of Classification Search
CPC ...... B01J 29/084; B01J 29/40; B01J 29/7007; B01J 29/7034; B01J 29/7038; B01J 29/08; B01J 29/085; B01J 29/16; B01J 29/405; B01J 29/48; B01J 29/7057; B01J 29/7084; B01J 29/7088; B01J 29/7815; B01J 29/7869; B01J 29/7876; B01J 2229/32; B01J 2229/42; B01J 2229/64; B01J 35/023; B01J 35/0013; B01J 37/04; B01J 37/341; Y10S 977/773; Y10S 977/779; C07C 2529/08; C07C 2529/12; C07C 2529/14; C07C 2529/16; C07C 2529/70; C07C 2529/74; C07C 2529/76; C07C 2529/78
USPC .......................................... 502/60, 63, 64, 66
See application file for complete search history.

(56) References Cited

U.S. PATENT DOCUMENTS

| | | | | |
|---|---|---|---|---|
| 4,499,318 A | * | 2/1985 | Liu .......................... | B01J 29/08 585/437 |
| 4,654,317 A | * | 3/1987 | Sachtler ................. | B01J 29/076 502/74 |
| 8,791,040 B2 | * | 7/2014 | Chinta ................... | B01J 29/068 502/60 |
| 2006/0264318 A1 | * | 11/2006 | Shan ........................ | B01J 21/06 502/60 |
| 2007/0227351 A1 | * | 10/2007 | Garcia-Martinez ...... | B01J 20/18 95/90 |
| 2008/0154083 A1 | * | 6/2008 | Gao ....................... | B01J 29/084 585/709 |

* cited by examiner

Primary Examiner — Elizabeth D Wood
(74) Attorney, Agent, or Firm — Albert Shung

(57) ABSTRACT

A catalyst containing nanosize zeolite particles supported on a support material for alkylation reactions, such as the alkylation of benzene to form ethylbenzene, and processes using such a catalyst is disclosed.

21 Claims, 3 Drawing Sheets

SUPPORTED NANO SIZED ZEOLITE CATALYST FOR ALKYLATION REACTIONS

CROSS-REFERENCE TO RELATED APPLICATIONS

This application is a Continuation of U.S. patent application Ser. No. 13/712,380, filed on Dec. 12, 2012; which claims priority to U.S. Provisional Patent Application No. 61/581,635, filed on Dec. 30, 2011; the entireties of which are incorporated herein by reference.

FIELD

The present disclosure is generally related to the alkylation of hydrocarbons. More specifically, the embodiments of the present disclosure relate to catalysts for the alkylation of hydrocarbons, such as the alkylation of benzene for the production of ethylbenzene and other compounds.

BACKGROUND

Styrene is an important monomer used in the manufacture of many polymers. Styrene is commonly produced by forming ethylbenzene, which is then dehydrogenated to produce styrene. Ethylbenzene is typically formed by one or more aromatic conversion processes involving the alkylation of benzene.

Aromatic conversion processes, which are generally carried out utilizing a molecular sieve type catalyst, are well known in the chemical processing industry. Such aromatic conversion processes include the alkylation of aromatic compounds such as benzene with ethylene to produce alkyl aromatics, such as ethylbenzene.

The molecular sieve catalysts that are suitable for use in these alkylation reactions typically include zeolites. The most commercially available zeolites are prepared such that the zeolite crystal is greater than 1 µm.

SUMMARY

Embodiments of the present disclosure include an alkylation catalyst having dispersed and/or grown nanosize zeolite particles and a support material. The support material can be selected from the group consisting of silica, silicon carbide, alumina, aluminosilica, titania, and zirconia, and combinations thereof The nanosize zeolite can have a particle size of less than 1000 nm or less than 300 nm and can be formed from a faujasite (FAU), such as an X-type or Y-type zeolite, MTW, MWW, BEA (beta) type zeolite or a MFI type zeolite, such as a ZSM-5, and other 10 membered and 12 membered ring zeolites. The support material can be selected from the group consisting of silica, alumina, including alpha alumina, alumina silicates, titania, and zirconia, and combinations thereof. The catalyst can further include a promoter selected from the group consisting of Co, Mn, Ti, Zr, Nb, K, Cs, Ga, P, B, Rb, Ge, Cu, Mg, Ce, Li, Ag, and Na and combinations thereof.

The catalyst and parts thereof can be hydrophilic in nature.

BRIEF DESCRIPTION OF DRAWINGS

The present disclosure is best understood from the following detailed description when read with the accompanying figures.

DETAILED DESCRIPTION

Figure 1:
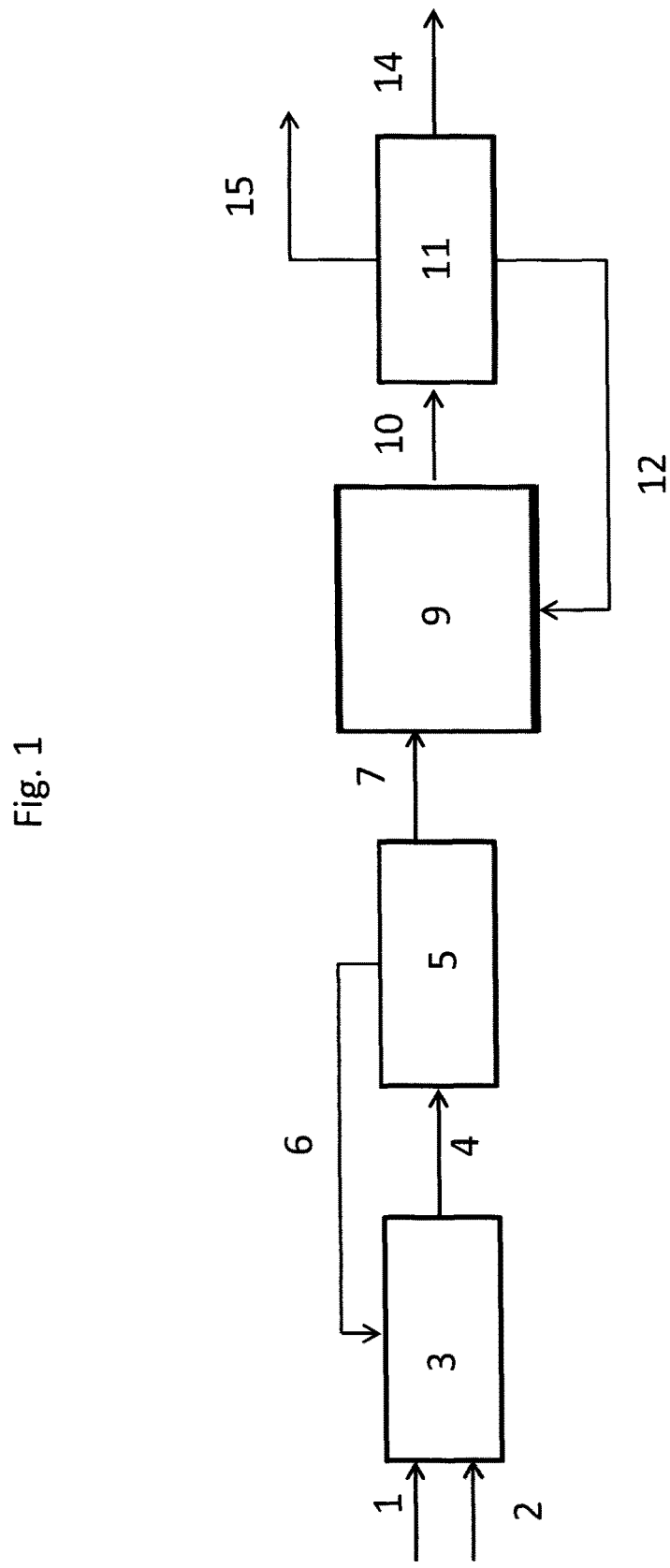
FIG. 1 illustrates a flow chart for the production of ethylbenzene by the alkylation reaction of benzene and ethylene consistent with at least one embodiment of the present disclosure.

The following disclosure provides many different embodiments, or examples, for implementing different features of various embodiments. Specific examples of components and arrangements are described below to simplify the present disclosure. These are, of course, merely examples and are not intended to be limiting.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Styrene production can include reacting benzene with ethylene to produce ethylbenzene that can then be dehydrogenated to form styrene. The catalysts described herein in combination with the described processes are capable of minimizing side product formation, thereby resulting in increased conversion and/or selectivity.

The styrene production process generally includes catalyst disposed within one or more reactors. The reactors may include fixed bed reactors, fluid bed reactors, entrained bed reactors or combinations thereof, for example. Reactors capable of operation at the elevated temperature and pressure as described herein, and capable of enabling contact of the reactants with the catalyst, can be considered within the scope of the present disclosure. Embodiments of the particular reactor system may be determined based on the particular design conditions and throughput, as by one of ordinary skill in the art, and are not meant to be limiting on the scope of the present disclosure.

In another embodiment, the one or more reactors may include one or more catalyst beds. When utilizing multiple beds, an inert material layer may separate each bed. In one or more embodiments, the reactor includes from 1 to 10 catalyst beds, or from 2 to 8 catalyst beds, or from 2 to 6 catalyst beds, for example.

In a non-limiting example, benzene and ethylene may be injected into a catalyst bed, an inert material layer or combinations thereof, for example.

In an embodiment, all of the benzene feed may flow through a series of catalyst beds and the ethylene may be injected between the catalyst beds to adjust the benzene:ethylene ratio for each catalyst bed to optimize conversion to ethylbenzene.

The operating conditions of the reactors will be system specific and can vary depending on the feedstream composition and the composition of the product streams. In one or more embodiments, the reactor(s) may operate at elevated temperatures and pressures, for example.

In one or more embodiments, the elevated temperature can range from 150° C. to 750° C., or from 175° C. to 500° C. or from 200° C. to 450° C., for example. The pressure can range from 0.1 atm to 70 atm, or from 0.1 atm to 35 atm, for example. In an embodiment, the reaction is conducted in a liquid phase and the elevated temperature can range from 150° C. to 400° C., or from 200° C. to 300° C. or from 200° C. to 260° C., for example. In an embodiment, the reaction is conducted in a gas phase and the elevated temperature can range from 300° C. to 750° C., or from 350° C. to 550° C. or from 400° C. to 460° C., for example.

FIG. 1 illustrates a simplified flow chart of one embodiment of the styrene production process described above. In this embodiment, a first reactor (3) is an alkylation reactor designed to react benzene feed (1) with an ethylene feed (2). The product stream (4) of the first reactor (3) may then be sent to a separation unit (5) where the ethylbenzene is separated from any unreacted benzene or ethylene and unwanted byproducts (6). Any unreacted benzene can then be recycled back into the first reactor (3). The byproducts and the benzene recycle steam (6) are separated from the ethylbenzene (7).

The ethylbenzene (7) in the presence of steam is then dehydrogenated to styrene in the dehydrogenation reactor (9). The styrene product (10) of the dehydrogenation reactor (9) may then be sent to a separation unit (11) where any unwanted byproducts (15), such as benzene, toluene, higher molecular weight compounds and water, can be separated from the styrene and unreacted ethylbenzene (12). Any unreacted ethylbenzene (12) can be recycled back into the dehydrogenation reactor (9). A styrene product stream (14) can be removed from the separation unit (11) and subjected to further treatment or processing if desired.

The catalyst utilized for the alkylation process described herein generally includes a zeolitic material. As used herein, the term "zeolitic material" refers to a molecular sieve containing an alumino silicate lattice. Zeolitic materials are well known in the art and possess well-arranged pore systems with uniform pore sizes.

Embodiments of the present disclosure utilize a nanosize zeolite. As used herein, the term "nanosize zeolite" refers to zeolitic materials having a particle size smaller than 5000 nm (5 μm), optionally smaller than 2500 nm (2.5 μm), optionally smaller than 1000 nm (1 μm). For example, the particle size may be less than 1000 nm, or less than 300 nm, or less 100 nm, or less than 50 nm, or less than 25 nm, for example. In one or more embodiments, the particle size is from 1.0 nm to 1000 nm, or from 10 nm to 500 nm, or from 25 nm to 300 nm, or from 50 nm to 100 nm, or from 20 nm to 200 nm, or from 50 nm to 75 nm, for example. As used herein, the "particle size" refers to either the size of each discrete crystal (i.e., crystal) of the zeolitic material or the size of an agglomeration of particles (i.e., crystallite) within the zeolitic material. The particles of nanosize zeolite may also be referred to as nanoparticles.

The zeolitic materials may include silicate-based zeolites, such as faujasites and mordenites, for example. Silicate-based zeolites may be formed of alternating Sift and $MO_x$ tetrahedra, where M is an element selected from the Groups 1 through 16 of the Periodic Table. Such formed zeolites may have 4, 6, 8, 10, or 12-membered oxygen ring channels, for example. An example of a faujasite are X-type and Y-type zeolites. Other suitable zeolitic materials may include MTW, FAU, or MWW. The zeolitic material may have a Si/Al ratio of 1.0 or greater. In an embodiment the Si/Al ratio can range from 1.0 to 300. In an alternate embodiment the Si/Al ratio can range from 1.0 to 100. In an alternate embodiment the Si/Al ratio can range from 1.0 to 50. In an alternate embodiment the Si/Al ratio can range from 1.0 to 25. The zeolitic material can include BEA type zeolite material such as beta zeolite, and MFI type zeolite material such as ZSM-5.

Optional support materials may include but not limited to silica, silicon carbide, alumina, including alpha alumina, alumina silicates, titania, zirconia and combinations thereof, for example. An optional support material can be a larger crystal size faujasite, such as a conventional sized zeolite, that can support a nanosize zeolite.

The catalyst generally includes from 1 wt. % to 99 wt. %, or from 3 wt. % to 90 wt. % or from 4 wt. % to 80 wt. % nanosize zeolite in the final catalyst, for example. In an embodiment the nanosize zeolite in the final catalyst ranges from 5 wt. % to 50 wt. %, optionally from 5 wt. % to 30 wt. %, optionally from 5 wt. % to 10 wt. %. In one or more embodiments, the catalyst includes from 5 wt. % to 20 wt. %, or from 5 wt. % to 15 wt. % or from 7 wt. % to 12 wt. %, optionally from 5 wt. % to 10 wt. % support material in the final catalyst, for example.

In one or more embodiments, the nanosize zeolite may have an increased ratio of surface area to volume compared to zeolitic materials that are not nanosize, for example. For example the nanosize zeolite may have at least 50% higher ratio of surface area to volume compared to zeolitic materials that are not nanosize, optionally at least 100% higher ratio, optionally at least two times higher ratio, optionally at least five times higher ratio, optionally at least ten times higher ratio.

The nanosize zeolite may be supported, or added, by any method(s) known to one skilled in the art. In an embodiment, these methods may include incipient wetness impregnation. In an alternative embodiment, the nanosize zeolite can be admixed with a support material. In a further embodiment, the nanosize zeolite may be supported in-situ with the support material or extruded. In an additional embodiment, the nanosize zeolite may be supported by spray-coating it onto a support material. It is further contemplated that such support processes may include layering the nanosize zeolite onto the support material, such as the support materials described below or optionally polymer spheres, such as polystyrene spheres, for example. It is even further contemplated that such support processes may include the utilization of zeolitic membranes, for example.

In one specific embodiment, the nanosize zeolite is supported by a support material and the nanosize zeolite is added to the support material via incipient wetness impregnation. In an embodiment, this process includes dispersing a nanosize zeolite in a diluent, such as non-limiting examples of methanol or toluene, to yield individually dispersed crystals, or individually dispersed nanoparticles. A support material may then be added to the solution and mixed until dry. In an embodiment, the dispersing of the nanoparticles of the nanosize zeolite in a solution is naturally dispersed or can be aided by agitation. Any suitable means of agitation can be used. In a specific embodiment, the agitation includes sonication.

In the incipient wetness impregnation method, the nanoparticles can have an affinity for one another and can form conglomerations inside the pores of the substrate. These conglomerations may become bound inside the support material, causing the nanosize zeolite to be supported by the support material. But conglomerations of the nanoparticles within the pores of the substrate are not necessary for the nanoparticles to be supported by the substrate.

In another embodiment, the nanoparticles may be added to the support aided by the use of carriers. In an embodiment, this process includes dispersing a nanosize zeolite in a diluent, such as methanol or toluene, to yield individually dispersed crystals, or individually dispersed nanoparticles. A support material may then be added to the solution and mixed. A carrier may be added to the solution at any point during the mixing. In an embodiment, the carrier is added to the diluent before the nanosize zeolite is added. In another embodiment, the carrier is added to the diluent after the nanosize zeolite is added and before the support material is added. In a further embodiment, the carrier is added after the nanosize zeolite and support material are added to the diluent. In an aspect, the zeolitic material, the catalytically active promoter, the support material or combinations thereof may optionally be contacted with a carrier prior to contact of the zeolitic material with the catalytically active promoter. This can be done by having an ion exchange, or other process of addition, performed after a supporting step. The carrier may be adapted to aid in the incorporation of the catalytically active promoter into the zeolitic material, for example. In one or more embodiments, the carrier is a nano-sized carrier, or nanocarrier (with the nano-sized carrier defined as for nanosize zeolites, as described above). In an embodiment, the carrier may include aluminum. In a more specific embodiment, the aluminum-containing carrier includes boehmite alumina. In an embodiment, the nanocarrier comprises material that can attract nanoparticles with columbic interaction.

In one embodiment, the nanosize zeolite is formed by utilizing a carrier to transport the nanosize zeolite into pores of the support material. In an embodiment, the carrier includes boehmite alumina. The carrier may be then be added to a solution containing a solvent. Boehmite alumina is a nano-sized crystallite having particle sizes from about 10 to 15 nm. These nanoparticles have a high surface charge that can adhere small particles, such as nano-zeolites, which can be beneficial in transporting the zeolites into the pores of the silica support material. The formed zeolite may then be dried and subjected to thermal treatment. During thermal treatment, the silica and alumina can bond and hold the zeolite in a cage-like assembly for catalytic activity. In a further embodiment, the carrier may be mixed with a solvent prior to contact with the nanosize zeolite.

In an embodiment, the nanosize zeolite is supported by physical addition of the nanosize zeolite with the zeolitic support. In another embodiment, the nanosize zeolite is supported by forming an extrudable material utilizing a support material in combination with the nanosize zeolite to form extrudates and/or tablets.

The nanosize zeolite may be chemically modified so that it will graft onto a support. In an embodiment, the nanosize zeolite is supported by surface modification of the nanosize zeolite followed by grafting the modified nanosize zeolite onto a support. In an embodiment, the support is selected from the group of silica, alumina, a monolith structure, silicon carbide, and combinations thereof. In another embodiment, the nanosize zeolite is supported by a process including: surface modifying the nanosize zeolites using a grafting molecule such as a silane (silica having functional groups) to yield a surface modified nanosize zeolite, wherein the surface modified nanosize zeolite has terminal reactive functional groups which can help to graft the nanosize zeolite onto a support.

In an embodiment the the catalyst is produced by a method that includes providing nanosize zeolite particles, contacting the nanosize zeolite particles with a silane resulting in a modified nanosize zeolite. The modified nanosize zeolite is then grafted onto a support and calcined resulting in a catalyst comprising nanosize zeolite particles.

In an embodiment, the nanosize zeolite is deposited or grown or grafted on a support by any suitable means, such as by non-limiting example one selected from the group of dip-coating, spray-coating, and wash-coating and any combinations thereof. The nanosize zeolite may be wash-coated on a monolith or an inert structured support for example.

The nanosize zeolite may be supported in situ with the support material. In an embodiment, the nanosize zeolite particles are created in situ with the support material. In another embodiment, the nanosize zeolite particles are simultaneously created and supported in situ with the support material.

The catalysts described herein may increase the effective diffusivity of the reactants, thereby increasing reactant conversion to desired products. Furthermore, the catalysts may result in processes exhibiting improved product selectivity over processes utilizing conventional zeolitic materials. In addition, activity of such processes may be increased due to an increase of accessibility of active sites, which thereby increases the effective number of active sites per weight of catalyst over larger non-nanosize zeolites.

Optionally, a catalytically active element, such as a catalytically active metal, may be incorporated into the nanosize zeolite by, for example, ion-exchange or impregnation of the zeolitic material, or by incorporating the active element in the synthesis materials from which the zeolitic material is prepared. As described herein, the term "incorporated into the zeolitic material" refers to incorporation into the framework of the zeolitic material, incorporation into channels of the zeolitic material (i.e., occluded) or combinations thereof.

The catalytically active element can be in a metallic form, combined with oxygen (e.g., metal oxide) or include derivatives of the compounds described below, for example. Suitable catalytically active metals depend upon the particular process in which the catalyst is intended to be used and generally include, but are not limited to, Co, Mn, Ti, Zr, Nb, K, Cs, Ga, P, B, Rb, Ge, Cu, Mg, Ce, and Na and combinations thereof.

In one or more embodiments, the nanosize zeolite may include less than 15 wt. % sodium of the total weight of active catalyst, optionally less than 7 wt. % sodium, optionally less than 1 wt. % sodium. In one or more embodiments, the nanosize zeolite may include less than 25 wt. % aluminum of the total weight of active catalyst, optionally less than 20 wt. % aluminum, optionally less than 7 wt. % aluminum. In one or more embodiments, the nanosize zeolite may include less than 30 wt. % silicon of the total weight of active catalyst, optionally less than 25 wt. % silicon, optionally less than 18 wt. % silicon. The balance of the nanosize zeolite will generally be formed of oxygen. If other elements are included in the material, then these amounts may be altered.

Aluminum oxide, commonly referred to as alumina, possesses strong ionic interatomic bonding giving rise to desirable material characteristics. It can exist in several crystalline phases which all revert to the most stable hexagonal alpha phase at elevated temperatures. Alpha phase alumina is the strongest and stiffest of the oxide ceramics. Its high hardness, refractoriness and good thermal properties make it the material of choice for a wide range of applications. High purity alumina is usable in both oxidizing and reducing atmospheres to 1925° C.

In an embodiment the nanosize zeolite catalyst can comprise alumina, optionally alpha, or beta, or delta, or theta phase alumina. In an embodiment the nanosize zeolite catalyst can comprise at least 5 wt. % alumina of the total weight of active catalyst, optionally at least 10 wt. % alumina, optionally at least 25 wt. % alumina, optionally at least 50 wt. % alumina.

Increased alkylation selectivity towards desired products may be achieved by treating the catalyst with chemical compounds to inhibit select basic sites. Such improvement may be accomplished by the addition of a second element. The second element can be one of those mentioned above. For example, in one or more embodiments, the second element may include boron.

A process for making ethylbenzene includes providing a $C_2$ source to a reactor containing a catalyst and reacting benzene with the $C_2$ source in the presence of the catalyst to form a product stream comprising ethylbenzene, wherein the catalyst includes nanosize zeolite particles. The $C_2$ source can be selected from the group consisting of ethanol, ethylene, and combinations thereof.

The processes described herein may exhibit an overall benzene conversion of at least 0.01 mol. %, or from 0.1 mol. % to 80 mol. %, or from 10 mol. % to 60 mol. % or from 15 mol. % to 40 mol. % for example.

The process may exhibit a selectivity to ethylbenzene of at least 5 mol. %, or from 5 mol. % to 99.9 mol. %, or at least 50 mol. % or at least 75 mol. %, for example.

EXAMPLES

Example 1

A supported nanosize zeolite material was prepared according to the incipient wetness impregnation method. In this method, 18 mg of nanozeolite (Cs/Y) having a size of about 60 nm were dispersed in toluene and then loaded on to 570 mg of silica support.

Figure 2:
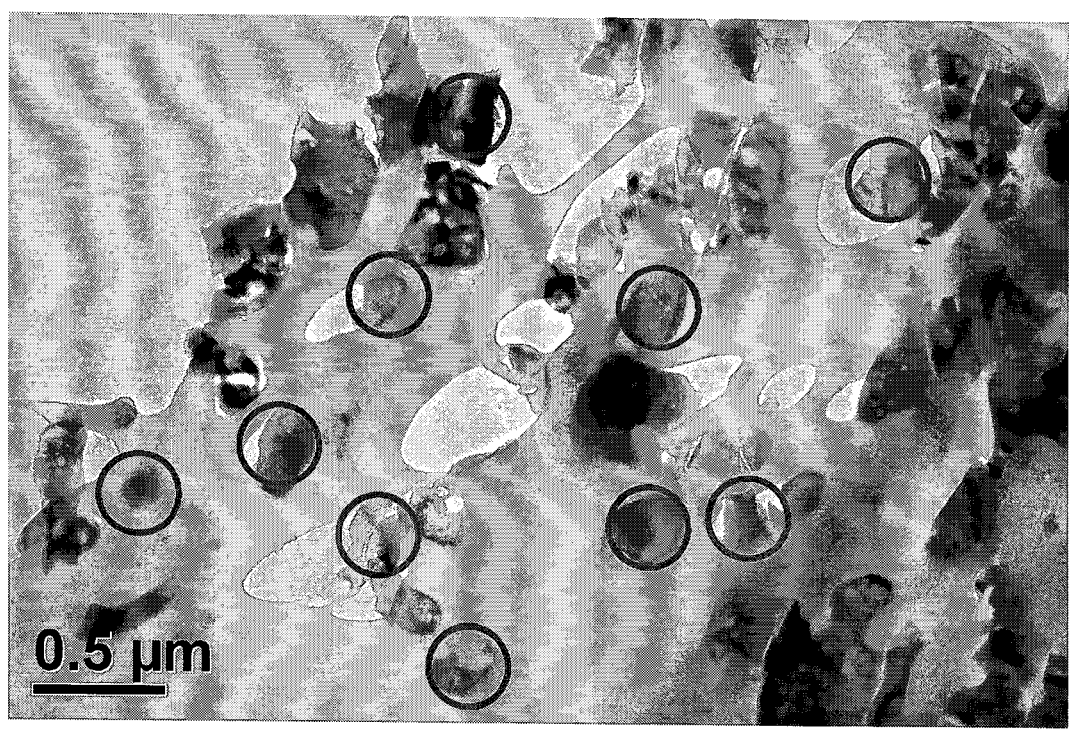
FIG. 2 is a Transmission Electron Microscopy (TEM) image of an embodiment of the present disclosure depicting nanozeolites incorporated in the pores of a silica substrate.

The Transmission Electron Microscopy (TEM) image in FIG. 2 shows that nanozeolites (Cs/Y), indicated by circles, are incorporated in the pores of the silica substrate and that they are well distributed.

Example 2

A supported nanosize zeolite material was prepared by utilizing nanocarriers. In this method, 2.18 g of nanozeolite (Cs/Y) having an average size as determined by TEM of about 60 nm were dispersed in 250 ml of toluene using sonication cycles creating a dispersion solution. Each sonication cycle was comprised of a five minute period at 450 watts and 21 amplitude level, followed by five minutes of inactivity to allow the solution to cool. This cycle was repeated three times, for a total of three cycles.

0.2 g of Catapal A alumina was added to the dispersion solution. Catapal A is a boehmite alumina, which is a nano-sized crystallite having sizes of about 10 to 15 nm. This boehmite alumina has a high surface charge that can adhere the small particles of the nanozeolites. The Catapal A is used as the nanocarrier. The mixture was then sonicated for five cycles.

10.09 g of silica having an average pore diameter of about 379 nm size as determined by TEM, a pore volume of 0.78 cc/g, and bulk density of 0.49 cc/g was then placed in an ion exchange column having an interior diameter of 1 inch. The dispersion solution was then added to the 10.09 g of silica in the ion exchange column. After the silica substrate was completely wet, the excess liquid was drained out and then left in a hood to air dry, followed by drying in a vented drying oven at 70° C. for 1 hr. This was repeated 19 times until the dispersion liquid was consumed.

The samples for TEM analysis were prepared by embedding the sample in an epoxy resin and curing the resin. The cured resin is then microtomed to ultra thin sections containing the cross-sections of the nanozeolites incorporated within the silica. The microtomed sections are placed on to the carbon film coated copper grid for TEM investigation.

Figure 3:
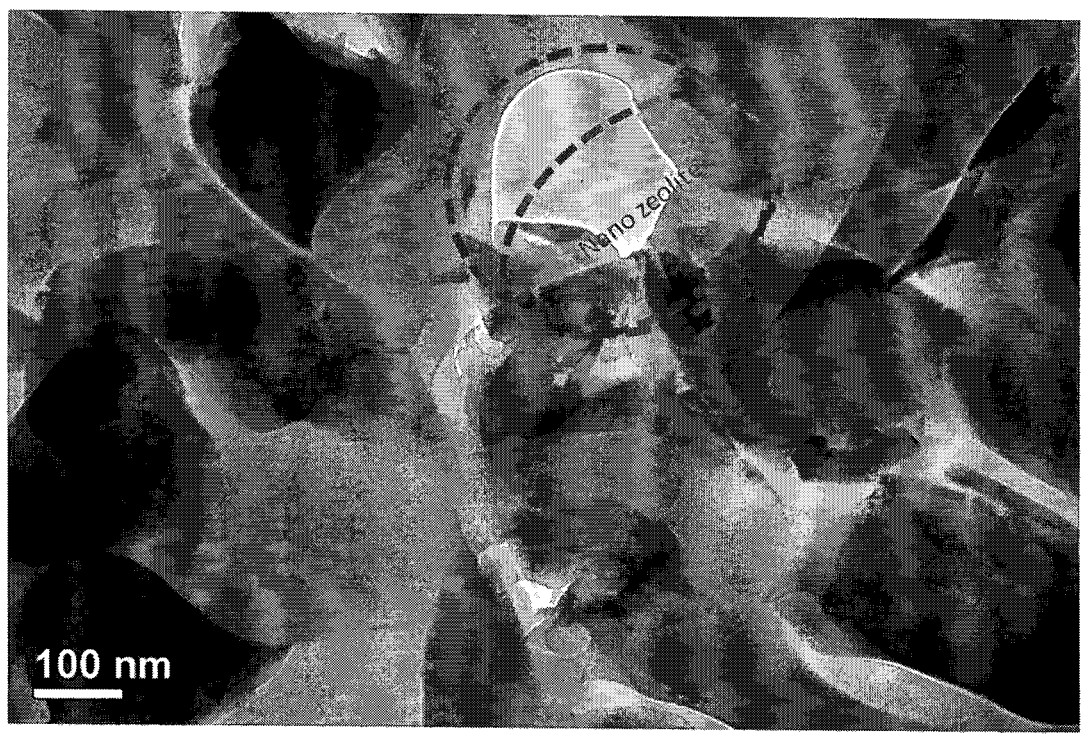
FIG. 3 is a TEM image of an embodiment of the present disclosure depicting distribution of nanocarriers and nanozeolites incorporated in the pores of a silica substrate.

The image in FIG. 3 shows distribution of nanocarriers (Catapal-A-alumina) as indicated by the larger dashed circle, along with the nanozeolites (Cs/Y), as indicated by the smaller dashed oval, incorporated in the pores of the silica substrate.

As used herein, the term "activity" refers to the weight of product produced per weight of the catalyst used in a process at a standard set of conditions per unit time.

The term "conversion" refers to the percentage of reactant (e.g. benzene) that undergoes a chemical reaction.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "selectivity" refers to the relative activity of a catalyst in reference to a particular compound in a mixture. Selectivity is quantified as the proportion of a particular product relative to all other products.

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present disclosure can be joined in combination with other embodiments of the disclosure and the listed embodiments herein are not meant to limit the disclosure. All combinations of embodiments of the disclosure are enabled, even if not given in a particular example herein.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure, and that they may make various changes, substitutions and alterations herein without departing from the spirit and scope of the present disclosure.

Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

While the foregoing is directed to embodiments, versions and examples of the present disclosure, which are included to enable a person of ordinary skill in the art to make and use the disclosures when the information in this patent is combined with available information and technology, the disclosure is not limited to only these particular embodiments, versions and examples. Also, it is within the scope of this disclosure that the aspects and embodiments disclosed herein are usable and combinable with every other embodiment and/or aspect disclosed herein, and consequently, this disclosure is enabling for any and all combinations of the embodiments and/or aspects disclosed herein. Other and further embodiments, versions and examples of the disclosure may be devised without departing from the basic scope thereof and the scope thereof is determined by the claims that follow.

What is claimed is:

1. A method for making a catalyst comprising:
   dispersing nanosize zeolite particles in a diluent;
   adding a support material to the diluent;
   adding a nanocarrier to the diluent wherein the nanocarrier comprises aluminum containing material; and
   mixing the diluent containing the nanosize zeolite particles, the support material, and the nanocarrier, wherein the nanocarrier transports the nanosize zeolite particles into pores of the support material.

2. The method of claim 1, wherein the aluminum containing material comprises boehmite alumina.

3. The method of claim 2, wherein the boehmite alumina is a nano-sized crystallite having particle sizes of from 10 to 15 nm.

4. The method of claim 1, wherein the nanosize zeolite particles, the support material, or combinations thereof are contacted with the nanocarrier prior to contact with a promoter.

5. The method of claim 4, wherein the promoter is selected from the group consisting of Co, Mn, Ti, Zr, Nb, K, Cs, Ga, P, B, Rb, Ge, Cu, Mg, Ce, Li, Ag, Na, and combinations thereof.

6. The method of claim 1, wherein the dispersing comprises sonication.

7. The method of claim 1, wherein the diluent is methanol or toluene.

8. The method of claim 1, wherein the catalyst comprises less than 15 weight percent sodium based on a total weight of the catalyst.

9. The method of claim 1, wherein the catalyst comprises less than 25 weight percent aluminum based on a total weight of the catalyst.

10. The method of claim 1, wherein the catalyst comprises less than 30 weight percent silicon based on a total weight of the catalyst.

11. The method of claim 1, wherein the catalyst comprises at least 5 weight percent alumina based on a total weight of the catalyst.

12. The method of claim 1, wherein the support material is selected from the group consisting of silica, silicon carbide, alumina, aluminosilica, titania, zirconia and combinations thereof.

13. The method of claim 1, wherein the nanosize zeolite particles are formed from a zeolite selected from the group consisting of FAU, BEA, MFI, MTW, FAU, MWW, and combinations thereof.

14. The method of claim 1, wherein the nanosize zeolite particles have a particle size of less than 1000 nm.

15. The method of claim 1, wherein the nanosize zeolite particles have a Si/Al ratio of 1.0 to 300.

16. The method of claim 1, wherein the catalyst comprises form 1 to 99 weight percent of the nanosize zeolite particles.

17. The method of claim 1, wherein the catalyst comprises from 5 to 20 weight percent of the support material.

18. The method of claim 1, wherein the nanocarrier is added to the diluent before the nanosize zeolite particles are added to the diluent.

19. The method of claim 1, wherein the nanocarrier is added to the diluent after the nanosize zeolite particles are added to the diluent and before the support material is added to the diluent.

20. The method of claim 1, wherein the nanocarrier is added to the diluent after the nanosize zeolite particles are added to the diluent and after the support material is added to the diluent.

21. The method of claim 1, wherein the nanocarrier has a particle size of less than 1000 nm.

* * * * *